US010543385B2

(12) United States Patent
Gao et al.

(10) Patent No.: US 10,543,385 B2
(45) Date of Patent: Jan. 28, 2020

(54) METHODS FOR EVALUATING THE STAIN REMOVAL EFFICACY OF DENTIFRICES

(71) Applicant: Colgate-Palmolive Company, New York, NY (US)

(72) Inventors: Yan Gao, Guangzhou (CN); Zhaoyu Wen, Guangzhou (CN); Guangxin Lin, Guangzhou (CN); Yun Xu, Langhorne, PA (US); Zhiping Zhong, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 26 days.

(21) Appl. No.: 15/523,777

(22) PCT Filed: Nov. 14, 2014

(86) PCT No.: PCT/CN2014/091095
§ 371 (c)(1),
(2) Date: May 2, 2017

(87) PCT Pub. No.: WO2016/074214
PCT Pub. Date: May 19, 2016

(65) Prior Publication Data
US 2018/0304102 A1 Oct. 25, 2018

(51) Int. Cl.
*A61Q 11/00* (2006.01)
*A61K 8/25* (2006.01)
*G01N 33/15* (2006.01)

(52) U.S. Cl.
CPC .............. *A61Q 11/00* (2013.01); *A61K 8/25* (2013.01); *G01N 33/15* (2013.01)

(58) Field of Classification Search
CPC ........... A61Q 11/00; A61K 8/25; G01N 33/15
See application file for complete search history.

(56) References Cited

U.S. PATENT DOCUMENTS

| 6,682,722 B2* | 1/2004 | Majeti | A61K 8/24 424/49 |
| 7,524,808 B2* | 4/2009 | Futterer | C11D 3/361 510/130 |
| 9,186,308 B2 | 11/2015 | Sakamoto | |
| 2005/0210615 A1 | 9/2005 | Shastry et al. | |
| 2006/0140882 A1* | 6/2006 | Tambs | A61K 8/22 424/53 |
| 2012/0244203 A1 | 9/2012 | Sakamoto | |
| 2013/0216487 A1* | 8/2013 | Lee | A61K 8/24 424/57 |

FOREIGN PATENT DOCUMENTS

| CN | 102655842 A | 9/2012 |
| JP | 2010-155785 | 7/2010 |
| KR | 1020140128500 | 4/2013 |
| WO | 2008/157197 | 12/2008 |

OTHER PUBLICATIONS

Coyle, 2008, "Which Toothpaste Whitens Teeth the Best?" TU-HHMI Science Academy Chemistry Modules pp. 1-5.
International Search Report and Written Opinion in International Application No. PCT/CN2014/091095, dated Jun. 26, 2015.
Katz, 2012, "Toothpaste," www.chymist.com.
Li, 2014, "Fluoride Toothpaste to Present Dental Caries Function Simulation in vitro—A recommendation for oral medical students," Chemistry Experiment Design Guangdong Chemical Industry 41(12):33 and 39.

* cited by examiner

*Primary Examiner* — Lezah Roberts

(57) ABSTRACT

Disclosed herein are methods for evaluating the whitening effect of oral care composition on a stained egg comprising staining an eggshell, applying the oral care composition to a portion of the stained eggshell to obtain a treated eggshell area, calculating a ΔE value for the difference in color of the treated eggshell area compared to untreated stained eggshell when calculated in L*a*b color space, wherein the oral care composition comprises at least one high cleaning silica for stain removal. Further disclosed herein are methods for demonstrating the whitening effect of an oral care composition on a stained egg comprising showing an egg that has been stained to at least one consumer and brushing an oral care composition comprising at least one high cleaning silica for stain removal on a portion of the stained eggshell to obtain a treated eggshell area.

6 Claims, 2 Drawing Sheets

METHODS FOR EVALUATING THE STAIN REMOVAL EFFICACY OF DENTIFRICES

BACKGROUND

There is a general desire in the population for people to have white or whiter teeth. Such white teeth are an indication of good health and in particular good oral health care. A problem is that various foods and the use of tobacco will discolor and stain teeth. Beverages such as coffee, tea, and soda can also discolor and stain teeth.

Scientists are continuously searching for effective teeth whitening and stain removal demonstrations to support marketing and scientific research needs. Several whitening demonstrations have been developed previously. One such demonstration uses stained sand dollars as a substrate to demonstrate the whitening efficacy of a particular toothpaste. The sand dollars are first stained and are then brushed with both the toothpaste being evaluated and a control toothpaste. The scientists and/or consumers may then visually compare the sand dollar(s) brushed with the two different toothpastes for different whitening effects in order to demonstrate higher whitening efficacy of a particular toothpaste. This demonstration may show the advantage of a toothpaste in removing both external and internal stains.

A second demonstration also uses stained shells as a substrate. The second demonstration aims to show that more stains may be removed from a stained shell by dipping the stained shell in a toothpaste slurry with agitation than by dipping it in a non-toothpaste solution with agitation. Since the toothpaste contains at least one surfactant and the non-toothpaste solution does not, the second demonstration aims to show that, with simple agitation, a toothpaste slurry with at least one surfactant may remove more stains than a non-toothpaste solution that does not contain surfactant.

It is desirable to develop further demonstrations in order to help evaluate the whitening and stain removal efficacy of new products and compositions, such as new toothpaste formulations, or to help aid consumer decisions about toothpaste purchases.

BRIEF SUMMARY

Disclosed herein are methods for evaluating the whitening effect of an oral care composition comprising staining an eggshell, applying the oral care composition to a portion of the stained eggshell to obtain a treated eggshell area, and calculating a ΔE value for the difference in color of the treated eggshell in L*a*b* color space, wherein the oral care composition comprises at least one high cleaning silica for stain removal.

In certain embodiments, the ΔE value is greater than about 15, such as greater than about 18 or greater than about 20. In certain other embodiments disclosed herein, at least one high cleaning silica for stain removal is present in the oral care composition in an amount ranging from about 1% to about 30% by weight, relative to the total weight of the composition, such as about 5% to about 25%, or about 10% to about 20%. In other embodiments disclosed herein, at least one high cleaning silica has an average particle size ranging from about 0.1 µm to about 30 µm, such as about 1 µm to about 20 µm, or about 5 µm to about 15 µm. In still further embodiments, the eggshell may be further stained with at least one of tea, soy sauce, soda, coffee, juice, and tobacco products.

Also disclosed herein are methods for demonstrating the whitening effect of an oral care composition on a stained egg comprising showing an egg that has been stained to at least one consumer, applying, for example, brushing, an oral care composition comprising at least one high cleaning silica for stain removal on a portion of the stained eggshell to obtain a first treated eggshell area, rinsing the egg with water, and showing to at least one consumer the first treated eggshell area, wherein the first treated eggshell area has an improved whitening effect as compared to either untreated stained egg or the stained egg area treated with regular toothpaste or water. As used herein, a regular toothpaste refers to any toothpaste that does not contain at least one high cleaning silica for stain removal. Further embodiments disclosed herein may comprise applying, for example brushing, a regular toothpaste or water on a second portion of the same stained eggshell to obtain a second treated eggshell area, and comparing the first treated eggshell area to the second treated eggshell area, wherein the first treated eggshell area has an improved whitening effect as compared to the second treated eggshell area.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1A:
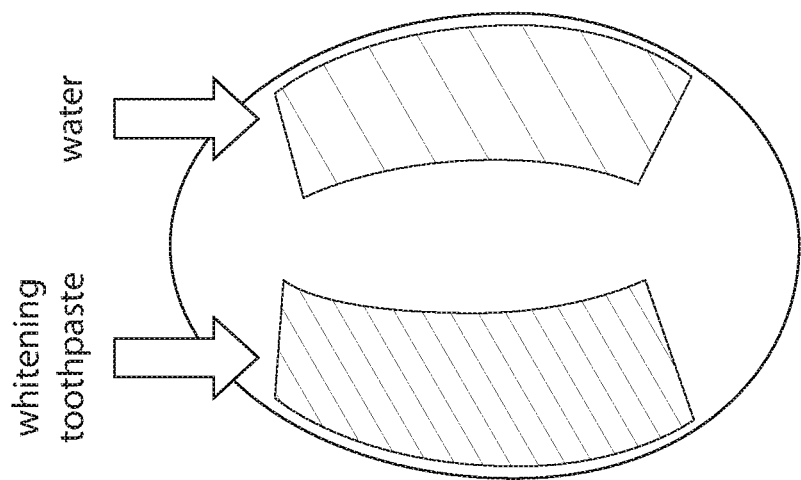
FIG. 1A is a picture showing a tea stained egg brushed with a whitening toothpaste comprising high cleaning silica on the left side and a regular toothpaste on the right side.

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents, and discoloring substances, such as coffee, tea, soda, juice, and tobacco agents, to permeate the enamel and discolor the tooth.

Stains associated with teeth are caused by the presence of chromophores (colored agents). These chromophores arise from two chemical sources—organic compounds, such as carotene, and inorganic transition metal ions, such as iron and tin, and combinations, such as blood having both iron and the colored porphyrin ligand. These stains can reside as extrinsic stains on the surface of the teeth and/or as intrinsic stains within the teeth. Extrinsic stain can be removed by abrasion and/or bleaching. However, intrinsic stains are bonded within the structure of the tooth and cannot be reduced by brushing or any abrasive process, but can only be reduced with a penetrating bleaching agent.

Extrinsic stain results from the binding of chromophores to the tooth surface by attractive forces such as electrostatic, van der Waals, and hydrogen bonding. Many foods and beverages contain staining chromophores that can deposit directly to the teeth. Tea, coffee, soda, and wine, for example, may contain darkly colored tannins that produce stain. Likewise, tobacco products can cause extrinsic stain. Calculus build up on the teeth can be perceived as extrinsic stain. Although calculus is naturally white, it can act as a reservoir to bind and trap chromophores from food and beverages. Similarly, the normally colorless plaque and pellicle can act as sites for binding staining chromophores to the teeth.

Disclosed herein are methods that use stained eggs as substrates to demonstrate that after brushing with an oral care composition, such as a toothpaste comprising at least one whitening ingredient, the stained egg is visibly whiter. In certain embodiments, the at least one whitening ingredient may be a high cleaning silica. In other methods disclosed herein, a stained egg may be used as a substrate to demonstrate that after brushing a first portion of the egg with a toothpaste comprising at least one whitening ingredient and after brushing a second portion of the egg with a regular (i.e., non-whitening) toothpaste, the first portion of the stained egg that has been brushed with the toothpaste comprising at least one whitening ingredient is visibly whiter than the second portion of the stained egg that has been brushed with the regular toothpaste. In yet another method disclosed herein, multiple stained eggs may be used as substrates to demonstrate that after brushing a first stained egg with a toothpaste comprising at least one whitening ingredient and after brushing a second egg with a regular toothpaste, the first stained egg that has been brushed with the toothpaste comprising at least one whitening ingredient is visibly whiter than the second stained egg that has been brushed with the regular toothpaste. After viewing such a demonstration, a consumer can better understand the whitening efficacy of a particular oral care composition.

A demonstration that uses stained eggs may be relevant to many consumers, for example consumers in China. Many Chinese people are familiar with or have eaten Tea Eggs (or stained eggs), so a demonstration using eggs may be more relevant to their lives than a demonstration using a different substrate.

In certain embodiments, it will be advantageous for the eggs used in the methods disclosed herein be large, white, and have a relatively uniform shape and size. Eggs should not have any damaged surface. The surface color of the egg should be uniform. Eggs may be excluded from demonstrations if there are any inherent visible stains or visible damaged surfaces, or if the eggs are damaged during experimentation. Also, it may be desirable to exclude eggs wherein the color of the surface of the stained egg is not adequately uniform.

In certain embodiments of the methods disclosed herein, use may be made of a plastic film comprising at least one open space as a brushing window, such as a rectangular or a circular open space. In certain embodiments the film may be adhesive, and in certain embodiments, the film comprises at least two open spaces as brushing windows.

In certain embodiments, the egg may be stained with at least one of tea, coffee, juice, soda, soy sauce, and tobacco products.

In one embodiment the eggs may be stained by contacting the eggs with tea. The tea may be of any concentration (i.e., ratio of tea leaves to liquid solution) in order to obtain a uniform stain of desired darkness. In certain embodiments, the eggs may be submerged in tea. In certain embodiments, the eggs may be stained with the tea for a sufficient period of time to allow the stain to develop to the desired level of darkness, such as, for example, about 1 hour or less, more than about 1 hour, about 5 hours to 10 hours, about 15 hours to about 20 hours, or about 18 hours. The tea may be at any temperature, including, for example, room temperature. In certain embodiments, in addition to tea or in place of tea, the egg may also be stained with at least one of coffee, juice, soda, soy sauce, and tobacco products.

In certain embodiments disclosed herein, after staining, an oral care composition comprising at least one whitening agent, such as at least one high cleaning silica, may be applied to a portion of the stained egg in order to obtain a first treated eggshell area. In other embodiments, a second oral care composition that does not contain a whitening agent may be applied to a second portion of the stained egg in order to obtain a second treated eggshell area. In some such embodiments, the two portions of the egg to which the oral care compositions are applied may be defined by the open spaces in the plastic film described above. In certain embodiments, there may either be no second treated eggshell area or the second treated eggshell area may be treated with only water. In certain other embodiments, an oral care composition may be applied to a first stained egg to obtain a first treated egg. In other embodiments, a second oral care composition that does not contain a whitening agent may be applied to a second stained egg in order to obtain a second treated egg. In certain embodiments, there may either be no second treated egg or the second egg may be treated with only water.

After treatment of the egg or eggs with an oral care composition comprising at least one whitening agent, the color of the treated eggshell areas or treated eggs may be measured for whiteness. The whiteness of the eggs may be measured by any means known in the art. In certain embodiments, whiteness of the eggs may be measured visually. Alternatively, whiteness can be measured by colorimetry, using any suitable instrument, such as a Minolta Chromameter, e.g., model CR-321 (Minolta Corp., Ramsey, N.J.) or an X-Rite SP60 Spectrophotometer. The colorimetry instrument can be programmed, for example, to measure Hunter Lab values or $L^*a^*b^*$ values according to the standard established by the International Committee of Illumination (CIE). The $L^*a^*b^*$ system provides a numerical representation of three-dimensional color space, wherein $L^*$ represents a lightness axis, $a^*$ represents a red-green axis, and $b^*$ represents a yellow-blue axis. The $L^*$ and $b^*$ axes are typically of greatest applicability to measurement of tooth whiteness. Increase in whiteness can be computed from differences in L*, a* and b* values before and after treatment, or between untreated and treated surfaces. In certain embodiments, a useful parameter may be ΔE, calculated as the square root of the sum of the squares of differences in L*, a* and b* values, using the formula: $\Delta E=[(\Delta L^*)^2+(\Delta a^*)^2+(\Delta b^*)^2]^{1/2}$. A higher value of ΔE indicates a greater increase in whiteness. In various embodiments, the methods disclosed herein can effect a ΔE of at least about 10, such as at least about 15, at least about 18, or at least about 20.

Abrasives such as high cleaning silicas can be used as an ingredient in toothpastes for whitening teeth. Abrasives in oral care compositions debride and physically scrub the external surface of the teeth. This scrubbing action removes organic biofilm (i.e., the pellicle) on the tooth surface that is formed primarily of salivary proteins, bacteria, and bacterial byproducts, thereby removing undesirable extrinsic stain. In this way, as used herein, a whitening effect is considered equivalent to stain removal. Further, such physical removal of the pellicle also removes plaque bacteria on the pellicle surface, thereby minimizing the potential for gingivitis, periodontitis, and caries formation. It is important to note, however, that oral care compositions such as dentifrices should not have such high abrasiveness that potential damage to the enamel or tissue may result. As such, it is desirable to develop oral care compositions that optimize the cleaning and/or polishing efficacy of the oral care composition, while minimizing any harmful abrasiveness to avoid potential damage to oral surfaces.

Any orally-acceptable abrasive can be used to enhance the whitening effect. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. In certain methods disclosed herein, the abrasive is a high cleaning silica abrasive. At least one abrasive, such as a high cleaning silica abrasive, is optionally present in the oral care composition with an abrasive effective total amount ranging from about 0.1% to about 40% by weight, such as from about 1% to about 10%, from about 2.5% to about 7%, or from about 2.5% to about 7%. In certain embodiments, the average particle size of the at least one abrasive may range from about 0.1 μm to about 30 μm, for example from about 1 μm to about 20 μm, or from about 5 μm to about 15 μm.

The hardness of a high cleaning silica abrasive can be expressed by a number of different tests known to those of skill in the art, including the Einlehner, Knoop, Vickers, and Rockwell hardness tests, as well as the Mohs scale of hardness. One method of evaluating abrasive particles is the Einlehner harness value. Einlehner hardness value is obtained using an Einlehner At –1000 Abrader to measure the softness of the abrasive particle in the following manner: a Fourdrinier brass wire screen is weighed and exposed to the action of a suspension of the abrasive (for example, a 10% aqueous suspension of the abrasive) for a given number of revolutions. The hardness value is expressed as milligrams weight lost of the Fourdrinier wire screen per 100,000 revolutions. Thus, in certain embodiments, the oral care composition may comprising at least one high cleaning silica abrasive having an Einlehner hardness of less than about 15 mg loss per 100,000 revolutions, such as less than about 10 mg loss per 100,000 revolutions, or less than about 5 mg loss per 100,000 revolutions. In certain embodiments, the at least one high cleaning silica has a hardness of less than or equal to that of the surface to be treated, such as the tooth or the eggshell.

The structure of an abrasive particle may also reflect abrasiveness; a relatively low structure tends to have higher abrasiveness and a relatively high structure abrasive tends to have lower abrasiveness. Particle structure may be indicated by absorption of linseed oil or dibutyl phthalate (DBP) per 100 grams. Oil absorption values can be measured using the ASTM Rub-Out Method D281.

In one embodiment the high cleaning silica is precipitated silica. The cleaning efficacy of the precipitated silica is expressed using the pellicle cleaning ratio (PCR). This is typically measured at 20% silica loading. The high cleaning silica preferably has a PCR value of greater than 85.

The efficacy of the precipitated silica can also be expressed with reference to its abrasive characteristic using the radioactive dentin abrasion (RDA). Ideally, RDA values for an oral composition should be below about 250 to protect tooth enamel/dentin.

Methods of performing PCR and RDA are described in e.g., U.S. Pat. Nos. 5,939,051 and 6,290,933 and "In Vitro Removal of Stain With Dentifrice", G. K. Stookey et al., J. Dental Research, Vol. 61, pages 1236-9, November 1982."

The one embodiment, the precipitated silica has a mean particle size $d_{50}$ of from 5 to 15 μm and an oil absorption of from 40 to 120 cm$^3$/100 g silica. Examples of precipitated silica having a mean particle size $d_{50}$ of from 5 to 15 μm and an oil absorption of from 40 to 120 cm$^3$/100 g silica including commercially available silicas such as Zeodent®103 and Zeodent®105 (Huber Silica Americas). In one embodiment, the high cleaning silica has an oil absorption structure of greater than about 90 cm$^3$/100 g. In various embodiments, the high cleaning silica particle has an oil absorption of greater than about 100 cm$^3$/100 g, or greater than about 110 cm$^3$/100 g.

In one embodiment, the high cleaning silica is precipitated silica having a pellicle cleaning ratio (PCR) of greater than 85 when tested at 20% silica loading. Preferably, the high cleaning silica also has a mean particle size $d_{50}$ of from 5 to 15 μm and an oil absorption of from 40 to 120 cm$^3$/100 g silica.

Particle size can be indicative of an abrasive's cleaning and/or polishing efficacy. Mean particle size can be measured by any means known in the art, including, for example, using a Malvern Particle Size Analyzer, Model Mastersizer S, Malvern Instruments, Inc. (Southborough, Mass., USA). With a Malvern Particle Size Analyzer, a helium-neon gas laser beam is projected through a transparent cell that contains the abrasive suspended in an aqueous solution. Light rays that strike the particles are scattered through angles that are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the subject abrasive.

In various embodiments, the at least one high cleaning silica may have a mean particle size of greater than about 8 μm, such as greater than about 10 μm. In some embodiments, the at least one high cleaning silica can have a mean particle size ranging from about 8 µm to about 14 µm.

Exemplary useful abrasive materials for preparing oral care compositions that may be used in accordance with the methods disclosed herein include high cleaning, low structure silica abrasives, such as those marketed under the trade names Sylodent® XWA or Sylodent® 783 by Davison Chemical Division of W. R. Grace & Co. (Baltimore, Md., USA). Sylodent® XWA 650 is a silica hydrogel composed of particles of colloidal silica.

Exemplary silica hydrogels comprise colloidal particles of silica having, in various embodiments, an average particle size ranging from about 3 µm to about 12 µm, such as from about 5 µm to about 10 µm, with a pH ranging from about 4 to about 10, such as from about 6 to about 9 when measured as a 5% by weight slurry. The particles of the XWA 650 contain about 10% to about 35% by weight water, have a mean particle size ranging from about 5 µm to about 12 µm, an Einlehner hardness of greater than or equal to about 5 mg to about 20 mg loss per 100,000 revolutions, an oil absorption of less than about 90 $cm^3$/100 g, for example from between about 40 $cm^3$/100 g to about 90 $cm^3$/100 g. The abrasives have a Brunauer, Emmett and Teller (BET) surface area of about 100 to about 700 $m^2$/g. XWA 650 has a brightness of 96.8 technidyne.

Another useful high cleaning silica abrasive is marketed as Sylodent® XWA 300 and is a silica hydrogel containing about 10% to about 25% water by weight, where the mean particle size ranges from about 2 µm to about 4 µm. The particles have BET surface area ranging from about 150 to about 400 $m^2$/g of silica. The XWA 300 abrasive has an oil absorption of less than 90 $cm^3$/100 g silica, and a pH, in a 5% w/w suspension in boiled ($CO_2$ free) demineralized water, equal to or greater than about 8.5.

In other embodiments, a high cleaning silica that may be used in accordance with the methods disclosed herein is a silica product, wherein the particles are about 5% to about 35% by weight water, having a mean particle size ranging from about 7 µm to about 11 µm, an Einlehner hardness of about 12 to about 19 and an oil absorption value of about 50 $cm^3$/100 g to about 65 $cm^3$/100 g. A BET surface area is about 100 to about 700 $m^2$/g of silica. The brightness is generally reported to be greater than about 95 technidyne. Such a silica product is commercially available as Zeodent® 105 from J. M. Huber (Havre de Grace, Md., USA).

Other useful abrasives include typical cleaning silica abrasives, such as precipitated silicas having a mean particle size of up to about 20 µm, such as from about 8 µm to about 14 µm, with an oil absorption structure of greater than about 90 to about 110 $cm^3$/100 g; for example, Zeodent® 115, marketed by J. M. Huber, that has a pH at 5% of the particles of about 6.5-7.5 and an Einlehner hardness of about 2 to 4 mg loss per 100,000 revolutions. The brightness of such a silica particle is greater than about 95.

In addition to the at least one high cleaning silica, the oral care compositions used in the methods disclosed herein may, in certain embodiments, further comprise at least one peroxide whitening agent, comprising at least one peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide.

In some embodiments disclosed herein, at least one non-peroxide whitening agent may be provided. Nonlimiting examples of whitening agents that may be mentioned include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. At least one whitening agent may optionally be present in a tooth-whitening effective total amount. In some embodiments the whitening agent may be separated from the aqueous carrier. In some embodiments the whitening agent is separated from the aqueous carrier by encapsulation of the whitening agent.

EXAMPLES

The study ran in a parallel design. Sixty (60) raw eggs were numbered 1-60 and were stained and evaluated. They were randomly assigned to two parallel groups—30 to one group, and other 30 to the other group.

A tea stain solution was prepared by steeping 36 Lipton black tea bags and 96 mL Lee Kum Kee dark soy sauce in 4800 mL deionized water at room temperature.

Eggs were chosen for the study were large, white, and had a relatively uniform shape and size. Eggs chosen did not have any visibly damaged surface and the color of the eggs appeared uniform. Eggs were purchased from the supermarket. All eggs were washed in tap water prior to use. Sixty raw eggs were used in the study.

First, all of the eggs were placed into the stain solution prepared as described above and boiled for 15 minutes. Then the eggs were placed in a room temperature environment, and the eggs continued to soak in the stain solution for 18 hours in order to acquire a dark stain. After 18 hours, the eggs were removed from the stain solution and tap water was used to wash the eggs in order to clean any impurities on the stained eggs' surfaces. Finally, the eggs were air dried on a dry surface.

All of the stained eggs were numbered 1-60 for identification purposes to monitor the stain removal. The labeled numbers were not visible for evaluators. The number was labeled on the top of each egg. Two white laminated films, each with a 15 mm×40 mm rectangular hole, were applied on two selected areas of each egg. The two areas were then labeled as "left side" and "right side" for each egg.

Before brushing, the selected areas of the eggs were evaluated for stain intensity. The color of each side of each stained egg was tested with an X-Rite SP60, in which L* is a measure of sample lightness, and a* is a measure of red/green, and b* is a measure of yellow/blue. The higher the L* value, the whiter the color. Six independent judges were asked to carefully evaluate if there was a difference between the two selected areas of each stained egg.

The 60 eggs were randomly grouped into two groups, one labeled Group 1 and one labeled Group 2. Group 1 was treated with whitening toothpaste comprising high cleaning silica (A) and a regular (i.e., non-whitening) toothpaste (B). Group 2 was treated with whitening toothpaste comprising high cleaning silica (A) and water (C) (i.e., the stained eggs were directly brushed with water in the absence of any toothpaste). Table 1 below identifies the eggs in each group.

TABLE 1

| Group 1: A (Whitening toothpaste containing High Cleaning Silica) & B (Regular Toothpaste) | | | | Group 2: A (Whitening toothpaste containing High Cleaning Silica) & C (Water) | | | |
|---|---|---|---|---|---|---|---|
| Egg 1 | B/left A/right | Egg 38 | A/left B/right | Egg 4 | A/left C/right | Egg 27 | A/left C/right |
| Egg 2 | A/left B/right | Egg 42 | B/left A/right | Egg 5 | C/left A/right | Egg 28 | C/left A/right |
| Egg 3 | B/left A/right | Egg 44 | A/left B/right | Egg 6 | A/left C/right | Egg 29 | C/left A/right |
| Egg 8 | A/left B/right | Egg 46 | B/left A/right | Egg 7 | C/left A/right | Egg 30 | A/left C/right |
| Egg 9 | B/left A/right | Egg 47 | B/left B/right | Egg 13 | A/left C/right | Egg 34 | C/left A/right |
| Egg 10 | A/left B/right | Egg 49 | B/left A/right | Egg 14 | C/left A/right | Egg 36 | A/left C/right |
| Egg 11 | B/left A/right | Egg 50 | B/left B/right | Egg 15 | A/left C/right | Egg 37 | C/left A/right |
| Egg 12 | A/left B/right | Egg 51 | B/left A/right | Egg 16 | C/left A/right | Egg 39 | A/left C/right |
| Egg 20 | B/left A/right | Egg 52 | A/left B/right | Egg 17 | A/left C/right | Egg 40 | C/left A/right |
| Egg 21 | A/left B/right | Egg 53 | A/left B/right | Egg 18 | C/left A/right | Egg 41 | A/left C/right |
| Egg 22 | B/left A/right | Egg 54 | B/left A/right | Egg 19 | A/left C/right | Egg 43 | C/left A/right |
| Egg 31 | A/left B/right | Egg 55 | A/left B/right | Egg 23 | C/left A/right | Egg 45 | A/left C/right |
| Egg 32 | B/left A/right | Egg 56 | B/left A/right | Egg 24 | C/left A/right | Egg 48 | C/left A/right |
| Egg 33 | A/left B/right | Egg 57 | A/left B/right | Egg 25 | A/left C/right | Egg 58 | A/left C/right |
| Egg 35 | B/left A/right | Egg 60 | B/left A/right | Egg 26 | C/left A/right | Egg 59 | C/left A/right |

Figure 1B:
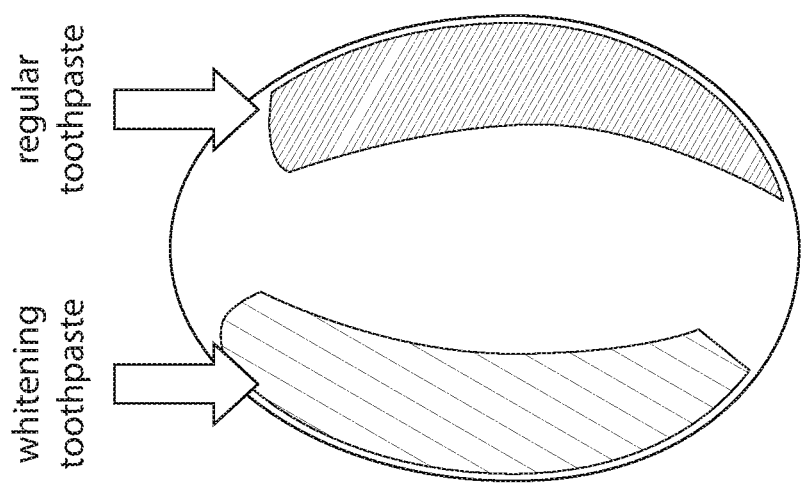
FIG. 1B is a picture showing a tea stained egg brushed with a whitening toothpaste comprising high cleaning silica on the left side and water on the right side.

For each egg in Group 1, if one side was brushed with whitening toothpaste containing high cleaning silica (HCS), then the other side was brushed with a regular toothpaste. For each egg in Group 2, if one side was brushed with whitening toothpaste containing HCS, then the other side was brushed without any toothpaste. In order to brush the egg, the 15 mm×40 mm rectangular hole on the eggshell that was not being brushed was manually covered, and only the selected brushing area was brushed (i.e., the other rectangular hole). For areas that were brushed with a toothpaste, 0.5 g of the toothpaste was used to brush the area. The area was brushed for 50 seconds using a soft bristle toothbrush. The brushing motion reciprocated from top to bottom and from bottom to top. After brushing, the treated stained egg was washed with tap water. Next the other side of the egg was brushed in the same manner, while manually covering the 15 mm×40 mm rectangular hole of the already brushed side of the stained egg. After the second brushing, the treated stained egg was again washed with tap water. Finally, the treated stained egg was air dried. FIG. 1A shows a picture of a sample egg from Group 1, wherein the egg was brushed with whitening toothpaste comprising HCS on the left side and the regular toothpaste on the right side. FIG. 1B shows a picture of a sample egg from Group 2, wherein the egg was brushed with whitening toothpaste comprising HCS on the left side and water on the right side.

The L*a*b* value of each treated side of each stained egg was tested. A panel of six judges was also asked to carefully evaluate the eggs and vote which treatment side of each stained egg was visibly whiter. The Paired Two Sample for Means t-test was used to calculate the statistical differences by analyzing the ΔE value, with a 95% confidence. The ΔE was calculated using the following equation: $\Delta E=[(\Delta L^{*2})+(\Delta a^{*2})+(\Delta b^{*2})]^{0.5}$, wherein ΔL=(L* after −L* before), Δa=(a* after −a* before), and Δb=(b* after −b* before). The higher the ΔE, the greater the whitening effect observed.

The L*a*b* values of the stained areas before brushing and the L*a*b* values of the stained areas after brushing are shown below in Table 2, wherein A indicates the area was brushed with whitening toothpaste containing HCS; B indicates the area was brushed with regular toothpaste; and C indicates the area was brushed with water.

TABLE 2

L*a*b* Values and ΔE Levels of Eggs after Staining and Brushing

| | | Before Brushing (stained eggs) | | | After Brushing | | | Result |
|---|---|---|---|---|---|---|---|---|
| | | L* | a* | b* | L* | a* | b* | (ΔE) |
| Group 1: Whitening toothpaste containing HCS and regular toothpaste | | | | | | | | |
| Egg 1 | B/left | 46.76 | 18.36 | 30.44 | 56.94 | 14.50 | 31.66 | 10.95 |
| | A/right | 46.99 | 18.56 | 30.82 | 68.41 | 11.00 | 29.57 | 22.75 |
| Egg 2 | A/left | 50.44 | 17.82 | 32.84 | 68.23 | 10.76 | 28.30 | 19.67 |
| | B/right | 51.90 | 17.87 | 34.46 | 63.69 | 12.35 | 30.60 | 13.58 |
| Egg 3 | B/left | 46.35 | 19.00 | 32.73 | 58.82 | 14.14 | 31.80 | 13.49 |
| | A/right | 45.27 | 19.29 | 32.12 | 65.34 | 12.28 | 29.81 | 21.39 |
| Egg 8 | A/left | 51.79 | 16.90 | 32.44 | 70.80 | 9.91 | 27.25 | 20.91 |
| | B/right | 51.51 | 17.00 | 32.70 | 65.65 | 11.24 | 28.51 | 15.82 |
| Egg 9 | B/left | 49.83 | 17.11 | 32.36 | 65.88 | 10.38 | 25.96 | 18.55 |
| | A/right | 50.90 | 16.92 | 31.90 | 72.79 | 8.61 | 23.97 | 24.71 |
| Egg 10 | A/left | 49.18 | 17.48 | 31.16 | 68.16 | 10.64 | 27.42 | 20.52 |
| | B/right | 48.62 | 18.06 | 32.64 | 64.35 | 11.53 | 28.34 | 17.57 |

TABLE 2-continued

L*a*b* Values and ΔE Levels of Eggs after Staining and Brushing

|  |  | Before Brushing (stained eggs) | | | After Brushing | | | Result |
|---|---|---|---|---|---|---|---|---|
|  |  | L* | a* | b* | L* | a* | b* | (ΔE) |
| Egg 11 | B/left | 46.91 | 17.82 | 29.88 | 61.35 | 11.55 | 28.24 | 15.83 |
|  | A/right | 48.54 | 18.08 | 32.24 | 70.22 | 9.42 | 26.90 | 23.94 |
| Egg 12 | A/left | 51.81 | 17.82 | 33.97 | 71.12 | 10.44 | 26.74 | 21.91 |
|  | B/right | 50.82 | 18.17 | 32.88 | 63.64 | 12.61 | 29.39 | 14.40 |
| Egg 20 | B/left | 52.94 | 16.08 | 33.20 | 66.53 | 10.15 | 27.60 | 15.85 |
|  | A/right | 53.24 | 15.60 | 31.58 | 71.90 | 8.71 | 26.39 | 20.55 |
| Egg 21 | A/left | 49.94 | 16.91 | 30.62 | 72.33 | 9.99 | 25.67 | 23.95 |
|  | B/right | 49.91 | 16.68 | 29.97 | 69.25 | 10.43 | 25.79 | 20.75 |
| Egg 22 | B/left | 51.19 | 16.99 | 31.92 | 66.19 | 10.84 | 27.69 | 16.75 |
|  | A/right | 50.39 | 16.82 | 31.44 | 69.77 | 9.60 | 26.31 | 21.31 |
| Egg 31 | A/left | 43.61 | 18.21 | 28.29 | 65.07 | 10.62 | 24.88 | 23.01 |
|  | B/right | 43.34 | 18.71 | 28.50 | 58.63 | 12.79 | 27.24 | 16.45 |
| Egg 32 | B/left | 43.81 | 18.44 | 28.86 | 61.86 | 12.12 | 27.61 | 19.17 |
|  | A/right | 44.14 | 18.64 | 30.05 | 67.45 | 10.74 | 25.93 | 24.95 |
| Egg 33 | A/left | 46.34 | 17.91 | 30.53 | 70.43 | 10.04 | 27.26 | 25.56 |
|  | B/right | 45.68 | 17.68 | 28.77 | 66.48 | 11.15 | 28.20 | 21.81 |
| Egg 35 | B/left | 46.58 | 17.51 | 28.47 | 57.42 | 13.69 | 29.34 | 11.52 |
|  | A/right | 47.12 | 17.74 | 29.42 | 68.98 | 10.59 | 27.10 | 23.11 |
| Egg 38 | A/left | 44.34 | 18.48 | 29.99 | 64.85 | 11.67 | 28.07 | 21.70 |
|  | B/right | 44.56 | 17.89 | 28.58 | 60.17 | 13.11 | 29.49 | 16.35 |
| Egg 42 | B/left | 47.38 | 17.06 | 29.61 | 65.03 | 11.50 | 28.43 | 18.55 |
|  | A/right | 46.84 | 17.59 | 29.62 | 70.50 | 10.42 | 27.36 | 24.83 |
| Egg 44 | A/left | 46.00 | 17.46 | 30.34 | 65.67 | 11.08 | 27.91 | 20.82 |
|  | B/right | 46.11 | 17.48 | 29.37 | 61.58 | 12.49 | 29.18 | 16.26 |
| Egg 46 | B/left | 46.83 | 16.44 | 29.09 | 62.15 | 11.49 | 27.84 | 16.15 |
|  | A/right | 47.77 | 16.51 | 29.54 | 70.30 | 9.91 | 27.08 | 23.61 |
| Egg 47 | A/left | 47.48 | 18.10 | 32.20 | 67.96 | 11.32 | 27.73 | 22.03 |
|  | B/right | 46.95 | 17.28 | 29.57 | 63.36 | 12.36 | 28.74 | 17.16 |
| Egg 49 | B/left | 46.71 | 17.56 | 30.79 | 62.42 | 11.90 | 28.69 | 16.83 |
|  | A/right | 47.85 | 16.49 | 29.04 | 69.23 | 10.34 | 27.34 | 22.31 |
| Egg 50 | A/left | 47.81 | 17.57 | 31.66 | 70.64 | 9.30 | 25.84 | 24.98 |
|  | B/right | 48.88 | 16.89 | 30.97 | 67.99 | 10.04 | 26.80 | 20.72 |
| Egg 51 | B/left | 46.73 | 16.65 | 28.79 | 62.62 | 11.73 | 27.97 | 16.65 |
|  | A/right | 46.81 | 17.19 | 30.41 | 70.21 | 9.62 | 26.65 | 24.89 |
| Egg 52 | A/left | 46.35 | 17.10 | 29.03 | 67.51 | 10.71 | 27.71 | 22.15 |
|  | B/right | 46.86 | 17.13 | 29.26 | 64.78 | 11.43 | 28.08 | 18.85 |
| Egg 53 | A/left | 44.83 | 17.11 | 26.52 | 70.07 | 9.09 | 26.96 | 26.49 |
|  | B/right | 45.44 | 17.93 | 29.12 | 64.60 | 11.09 | 28.58 | 20.35 |
| Egg 54 | B/left | 46.75 | 17.47 | 30.59 | 64.83 | 10.99 | 27.57 | 19.44 |
|  | A/right | 46.78 | 17.20 | 31.24 | 70.03 | 8.99 | 25.55 | 25.30 |
| Egg 55 | A/left | 46.50 | 17.59 | 29.17 | 66.09 | 11.86 | 29.09 | 20.42 |
|  | B/right | 46.30 | 17.15 | 29.11 | 64.67 | 11.89 | 29.79 | 19.12 |
| Egg 56 | B/left | 44.80 | 17.25 | 26.48 | 64.82 | 11.93 | 28.25 | 20.79 |
|  | A/right | 44.76 | 17.33 | 27.06 | 71.95 | 9.89 | 26.11 | 28.21 |
| Egg 57 | A/left | 47.25 | 17.05 | 31.04 | 67.54 | 10.18 | 27.10 | 21.78 |
|  | B/right | 47.83 | 17.00 | 30.85 | 64.26 | 11.28 | 28.13 | 17.60 |
| Egg 60 | B/left | 45.88 | 16.68 | 29.02 | 58.61 | 13.04 | 29.95 | 13.27 |
|  | A/right | 46.38 | 17.20 | 29.28 | 71.43 | 9.06 | 25.80 | 26.57 |
| Group 2: Whitening toothpaste containing HCS and water | | | | | | | | |
| Egg 4 | A/left | 46.11 | 18.95 | 32.04 | 68.89 | 9.92 | 26.71 | 25.08 |
|  | C/right | 46.18 | 18.52 | 31.54 | 53.84 | 14.38 | 29.09 | 9.05 |
| Egg 5 | C/left | 46.31 | 18.50 | 30.58 | 52.46 | 15.05 | 29.61 | 7.13 |
|  | A/right | 45.55 | 19.17 | 32.52 | 65.64 | 11.18 | 28.54 | 21.99 |
| Egg 6 | A/left | 48.72 | 17.52 | 31.87 | 70.88 | 9.05 | 25.24 | 24.63 |
|  | C/right | 48.57 | 17.70 | 32.00 | 57.76 | 12.08 | 26.73 | 11.99 |
| Egg 7 | C/left | 49.48 | 17.42 | 31.57 | 52.95 | 14.47 | 28.74 | 5.36 |
|  | A/right | 49.55 | 17.48 | 32.35 | 69.74 | 9.81 | 27.13 | 22.22 |
| Egg 13 | A/left | 47.46 | 16.44 | 30.06 | 66.02 | 10.26 | 27.77 | 19.69 |
|  | C/right | 47.52 | 16.45 | 30.09 | 54.56 | 13.26 | 29.23 | 7.78 |
| Egg 14 | C/left | 48.92 | 17.87 | 32.31 | 52.29 | 14.51 | 28.45 | 6.13 |
|  | A/right | 50.54 | 17.30 | 32.33 | 70.38 | 8.87 | 25.09 | 22.74 |
| Egg 15 | A/left | 49.38 | 16.44 | 29.55 | 68.93 | 9.90 | 25.84 | 20.95 |
|  | C/right | 49.20 | 16.51 | 29.73 | 55.61 | 12.84 | 26.91 | 7.90 |
| Egg 16 | C/left | 49.92 | 17.07 | 32.11 | 56.75 | 13.24 | 28.06 | 8.82 |
|  | A/right | 50.75 | 16.81 | 32.43 | 72.61 | 8.61 | 24.86 | 24.54 |
| Egg 17 | A/left | 48.21 | 17.28 | 31.44 | 68.99 | 9.69 | 26.95 | 22.57 |
|  | C/right | 48.80 | 17.45 | 32.03 | 54.94 | 13.54 | 29.13 | 7.84 |
| Egg 18 | C/left | 53.55 | 15.10 | 31.72 | 63.17 | 10.71 | 27.36 | 11.44 |
|  | A/right | 52.72 | 15.74 | 31.20 | 72.00 | 7.82 | 24.51 | 21.89 |
| Egg 19 | A/left | 51.44 | 17.21 | 33.43 | 71.11 | 9.31 | 27.39 | 22.04 |
|  | C/right | 51.47 | 16.96 | 33.11 | 61.18 | 11.78 | 29.39 | 11.62 |

TABLE 2-continued

L*a*b* Values and ΔE Levels of Eggs after Staining and Brushing

|  |  | Before Brushing (stained eggs) | | | After Brushing | | | Result |
|---|---|---|---|---|---|---|---|---|
|  |  | L* | a* | b* | L* | a* | b* | (ΔE) |
| Egg 23 | A/left | 50.55 | 16.21 | 30.72 | 70.80 | 8.94 | 25.02 | 22.26 |
|  | C/right | 49.52 | 16.61 | 30.69 | 59.17 | 12.02 | 27.69 | 11.10 |
| Egg 24 | C/left | 49.05 | 17.54 | 32.40 | 57.33 | 12.99 | 28.97 | 10.05 |
|  | A/right | 49.95 | 17.06 | 31.54 | 74.44 | 8.03 | 24.92 | 26.93 |
| Egg 25 | A/left | 52.81 | 16.49 | 32.95 | 74.97 | 7.53 | 24.26 | 25.43 |
|  | C/right | 52.37 | 16.79 | 34.02 | 62.54 | 11.68 | 28.99 | 12.44 |
| Egg 26 | C/left | 52.16 | 16.45 | 31.25 | 58.14 | 13.43 | 30.41 | 6.75 |
|  | A/right | 51.38 | 17.28 | 32.96 | 71.62 | 9.83 | 27.41 | 22.27 |
| Egg 27 | A/left | 52.40 | 16.27 | 32.34 | 69.34 | 9.90 | 26.96 | 18.88 |
|  | C/right | 51.46 | 16.56 | 31.72 | 58.33 | 12.86 | 29.51 | 8.11 |
| Egg 28 | C/left | 51.04 | 17.15 | 32.44 | 59.79 | 12.54 | 29.94 | 10.20 |
|  | A/right | 50.47 | 17.21 | 33.09 | 73.60 | 8.50 | 26.06 | 25.69 |
| Egg 29 | C/left | 47.98 | 17.76 | 30.81 | 58.72 | 13.04 | 30.23 | 11.74 |
|  | A/right | 48.51 | 17.64 | 31.13 | 69.23 | 10.12 | 27.26 | 22.38 |
| Egg 30 | A/left | 50.64 | 17.05 | 32.67 | 69.05 | 10.18 | 28.12 | 20.17 |
|  | C/right | 51.36 | 16.92 | 32.17 | 60.05 | 12.30 | 29.85 | 10.11 |
| Egg 34 | C/left | 49.30 | 18.83 | 35.17 | 53.46 | 15.97 | 32.27 | 5.82 |
|  | A/right | 50.01 | 18.29 | 33.06 | 66.96 | 12.04 | 29.82 | 18.36 |
| Egg 36 | A/left | 44.98 | 18.36 | 30.12 | 64.26 | 11.64 | 28.80 | 20.46 |
|  | C/right | 44.66 | 18.11 | 29.18 | 49.62 | 15.13 | 28.16 | 5.88 |
| Egg 37 | C/left | 46.68 | 16.72 | 29.11 | 55.49 | 13.36 | 29.18 | 9.43 |
|  | A/right | 47.29 | 16.85 | 29.77 | 70.96 | 9.10 | 27.94 | 24.98 |
| Egg 39 | A/left | 45.51 | 17.68 | 29.66 | 69.62 | 10.12 | 27.55 | 25.36 |
|  | C/right | 45.35 | 18.07 | 31.10 | 52.96 | 14.73 | 29.44 | 8.47 |
| Egg 40 | C/left | 44.02 | 17.90 | 29.15 | 49.67 | 14.96 | 27.44 | 6.59 |
|  | A/right | 44.73 | 17.78 | 29.81 | 67.82 | 9.48 | 25.34 | 24.94 |
| Egg 41 | A/left | 50.41 | 16.59 | 31.88 | 70.09 | 9.81 | 27.55 | 21.26 |
|  | C/right | 50.38 | 16.67 | 32.20 | 58.36 | 13.09 | 29.57 | 9.14 |
| Egg 43 | C/left | 49.23 | 17.05 | 29.52 | 54.47 | 15.29 | 30.08 | 5.56 |
|  | A/right | 48.19 | 17.25 | 28.46 | 65.10 | 13.15 | 29.23 | 17.42 |
| Egg 45 | A/left | 45.86 | 17.28 | 29.37 | 69.87 | 9.11 | 25.18 | 25.71 |
|  | C/right | 45.55 | 17.64 | 29.98 | 49.85 | 14.88 | 27.96 | 5.50 |
| Egg 48 | C/left | 50.00 | 16.40 | 30.17 | 53.25 | 14.86 | 29.59 | 3.64 |
|  | A/right | 49.41 | 16.93 | 31.24 | 68.56 | 10.38 | 27.75 | 20.53 |
| Egg 58 | A/left | 45.73 | 17.12 | 29.13 | 66.73 | 10.69 | 27.71 | 22.01 |
|  | C/right | 45.64 | 17.03 | 28.20 | 52.41 | 14.27 | 28.75 | 7.33 |
| Egg 59 | C/left | 44.39 | 18.17 | 29.43 | 55.98 | 14.02 | 29.38 | 12.32 |
|  | A/right | 44.75 | 17.99 | 29.70 | 67.60 | 11.63 | 28.09 | 23.77 |

Figure 2:
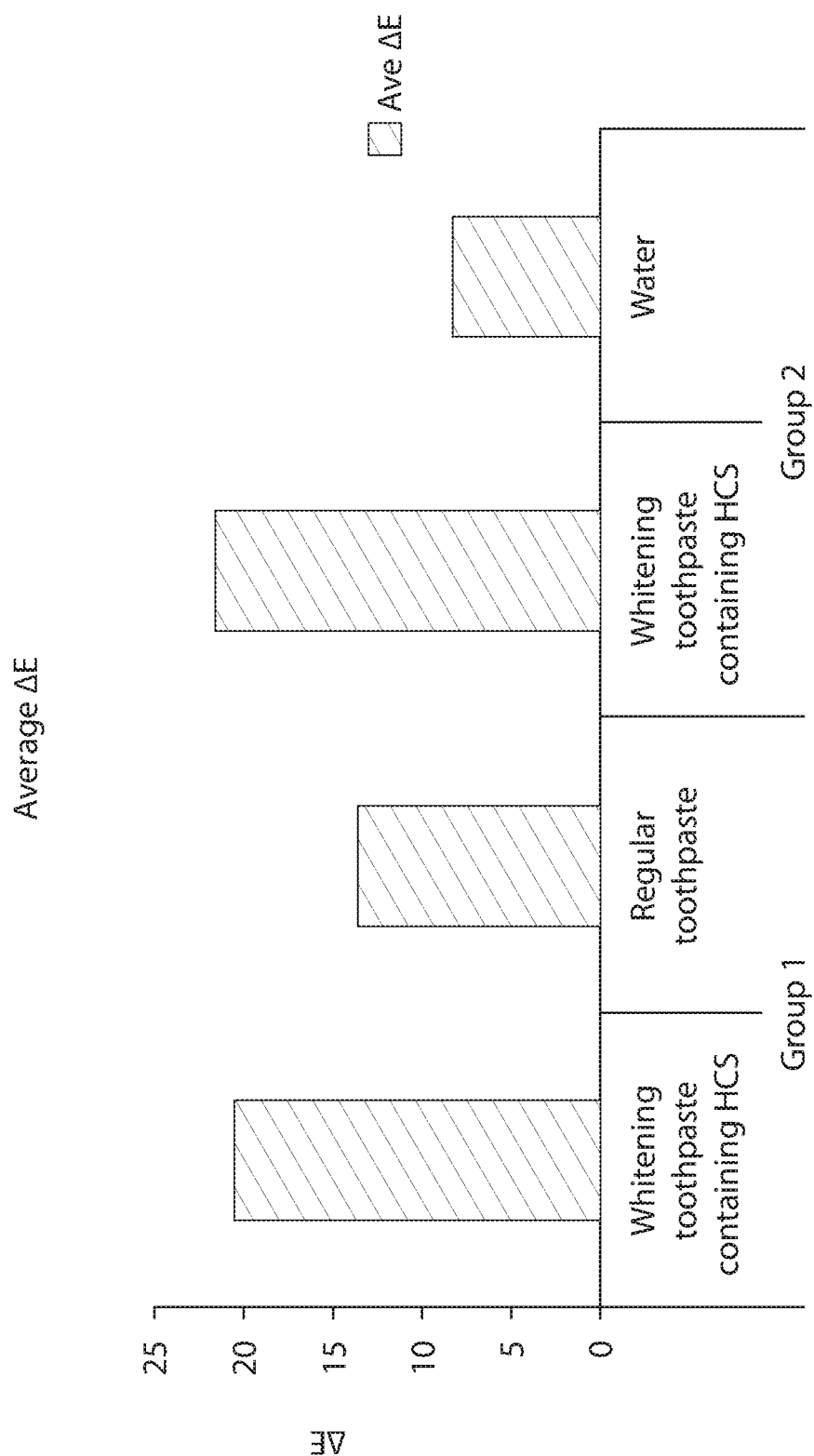
FIG. 2 is a bar graph showing the average ΔE for tea stained eggs brushed with a whitening toothpaste comprising high cleaning silica in a first group of eggs; tea stained eggs brushed with a regular toothpaste in a first group of eggs; tea stained eggs brushed with a whitening toothpaste comprising high cleaning silica in a second group of eggs; and tea stained eggs brushed with water.

Table 3 below shows the average ΔE values and the results of the statistical analyses. The results from Group 1 indicate that there is a significant difference between whitening toothpaste containing HCS and regular toothpaste. Likewise, the results from Group 2 indicate that there is a significant difference between whitening toothpaste containing HCS and water. FIG. 2 is a bar graph illustrating the average ΔE for stained tea eggs. As shown in the FIG. 2 and in Table 3 below, for the stained eggs in Group 1 brushed with a whitening toothpaste comprising high cleaning silica in a first group of eggs, the ΔE was 20.42. For the stained tea eggs in Group 1 brushed with a regular toothpaste, the ΔE was 13.44. For the stained tea eggs brushed with a whitening toothpaste comprising high cleaning silica in Group 2, the ΔE was 21.5, and for the stained tea eggs brushed with water in Group 2, the ΔE was 8.22. Accordingly, the highest ΔEs of 20.42 and 21.5 were obtained by brushing with whitening toothpaste comprising high cleaning silica. Statistically significant lower ΔEs of 13.44 and 8.22 were obtained by brushing with regular toothpaste and water, respectively.

TABLE 3

|  |  | Average ΔE | P (95% Confidence) |
|---|---|---|---|
| Group 1 | Whitening toothpaste containing HCS | 20.42 | P(one-tail) = 2.7 * 10^-13 < 0.05 |

TABLE 3-continued

|  |  | Average ΔE | P (95% Confidence) |
|---|---|---|---|
|  | Regular toothpaste | 13.44 | P(two-tail) = 5.4 * 10^-13 < 0.05 |
| Group 2 | Whitening toothpaste containing HCS | 21.5 | P(one-tail) = 3.54 * 10^-23 < 0.05 |
|  | Water | 8.22 | P(two-tail) = 7.09 * 10^-23 < 0.05 |

This demonstrates that whitening toothpaste comprising HCS has a higher stain removal efficacy compared to both regular toothpaste and water. Statistical analysis shows that the difference between the ΔE of the whitening toothpaste comprising HCS and the ΔE of regular toothpaste is a statistically significant (P value is less than 0.05 with 95% confidence), as is the difference between whitening toothpaste comprising HCS and water.

Next, six independent judges assessed the results of the treatment of the stained eggs. For the eggs in Group 1, all of the judges ranked the sides brushed with whitening toothpaste comprising HCS visibly whiter than the sides brushed with regular toothpaste. Similarly, for the eggs in Group 2, all of the judges ranked the sides brushed with whitening toothpaste comprising HCS whiter than the sides brushed with water. These qualitative results are consistent with those of the quantitative Chromatic Aberration test, which demonstrated that whitening toothpaste comprising HCS gave greater ΔE thus higher stain removal efficacy compared to water and regular toothpaste. The results of the independent judges are shown below in Table 4, below, wherein "Y" indicates which side of the egg the judges determined to be whiter.

It can be concluded from the judges' visual inspections of the eggs that the qualitative results are consistent with those of the quantitative Chromatic Aberration test, which demonstrated that whitening toothpaste comprising HCS yielded a greater ΔE, and thus has a high stain removal efficacy as compared to water and regular toothpaste.

TABLE 4

Stain Intensity Assessment

| After brushing | | Judge 1 | Judge 2 | Judge 3 | Judge 4 | Judge 5 | Judge 6 |
|---|---|---|---|---|---|---|---|
| Group 1 (A and B) | | | | | | | |
| Egg 1 | B/left | | | | | | |
| | A/right | Y | Y | Y | Y | Y | Y |
| Egg 2 | A/left | Y | Y | Y | Y | Y | Y |
| | B/right | | | | | | |
| Egg 3 | A/left | Y | Y | Y | Y | Y | Y |
| | B/right | | | | | | |
| Egg 8 | A/left | Y | Y | Y | Y | Y | Y |
| | B/right | | | | | | |
| Egg 9 | B/left | | | | | | |
| | A/right | Y | Y | Y | Y | Y | Y |
| Egg 10 | A/left | Y | Y | Y | Y | Y | Y |
| | B/right | | | | | | |
| Egg 11 | B/left | | | | | | |
| | A/right | Y | Y | Y | Y | Y | Y |
| Egg 12 | A/left | Y | Y | Y | Y | Y | Y |
| | B/right | | | | | | |
| Egg 20 | B/left | | | | | | |
| | A/right | Y | Y | Y | Y | Y | Y |
| Egg 21 | A/left | Y | Y | Y | Y | Y | Y |
| | B/right | | | | | | |
| Egg 22 | B/left | | | | | | |
| | A/right | Y | Y | Y | Y | Y | Y |
| Egg 31 | A/left | Y | Y | Y | Y | Y | Y |
| | B/right | | | | | | |
| Egg 32 | B/left | | | | | | |
| | A/right | Y | Y | Y | Y | Y | Y |
| Egg 33 | A/left | Y | Y | Y | Y | Y | Y |
| | B/right | | | | | | |
| Egg 35 | B/left | | | | | | |
| | A/right | Y | Y | Y | Y | Y | Y |
| Egg 38 | A/left | Y | Y | Y | Y | Y | Y |
| | B/right | | | | | | |
| Egg 42 | B/left | | | | | | |
| | A/right | Y | Y | Y | Y | Y | Y |
| Egg 44 | A/left | Y | Y | Y | Y | Y | Y |
| | B/right | | | | | | |
| Egg 46 | B/left | | | | | | |
| | A/right | Y | Y | Y | Y | Y | Y |
| Egg 47 | A/left | Y | Y | Y | Y | Y | Y |
| | B/right | | | | | | |
| Egg 49 | B/left | | | | | | |
| | A/right | Y | Y | Y | Y | Y | Y |
| Egg 50 | A/left | Y | Y | Y | Y | Y | Y |
| | B/right | | | | | | |
| Egg 51 | B/left | | | | | | |
| | A/right | Y | Y | Y | Y | Y | Y |
| Egg 52 | A/left | Y | Y | Y | Y | Y | Y |
| | B/right | | | | | | |
| Egg 53 | A/left | Y | Y | Y | Y | Y | Y |
| | B/right | | | | | | |
| Egg 54 | B/left | | | | | | |
| | A/right | Y | Y | Y | Y | Y | Y |
| Egg 55 | A/left | Y | Y | Y | Y | Y | Y |
| | B/right | | | | | | |
| Egg 56 | B/left | | | | | | |
| | A/right | Y | Y | Y | Y | Y | Y |
| Egg 57 | A/left | Y | Y | Y | Y | Y | Y |
| | B/right | | | | | | |
| Egg 60 | B/left | | | | | | |
| | A/right | Y | Y | Y | Y | Y | Y |
| Result: | | 100% A > B | | | | | |
| Group 2 (A and C) | | | | | | | |
| Egg 4 | A/left | Y | Y | Y | Y | Y | Y |
| | C/right | | | | | | |
| Egg 5 | C/left | | | | | | |
| | A/right | Y | Y | Y | Y | Y | Y |
| Egg 6 | A/left | Y | Y | Y | Y | Y | Y |
| | C/right | | | | | | |
| Egg 7 | C/left | | | | | | |
| | A/right | Y | Y | Y | Y | Y | Y |
| Egg 13 | A/left | Y | Y | Y | Y | Y | Y |
| | C/right | | | | | | |
| Egg 14 | C/left | | | | | | |
| | A/right | Y | Y | Y | Y | Y | Y |
| Egg 15 | A/left | Y | Y | Y | Y | Y | Y |
| | C/right | | | | | | |
| Egg 16 | C/left | | | | | | |
| | A/right | Y | Y | Y | Y | Y | Y |
| Egg 17 | A/left | Y | Y | Y | Y | Y | Y |
| | C/right | | | | | | |
| Egg 18 | C/left | | | | | | |
| | A/right | Y | Y | Y | Y | Y | Y |
| Egg 19 | A/left | Y | Y | Y | Y | Y | Y |
| | C/right | | | | | | |
| Egg 23 | A/left | Y | Y | Y | Y | Y | Y |
| | C/right | | | | | | |
| Egg 24 | C/left | | | | | | |
| | A/right | Y | Y | Y | Y | Y | Y |
| Egg 25 | A/left | Y | Y | Y | Y | Y | Y |
| | C/right | | | | | | |
| Egg 26 | C/left | | | | | | |
| | A/right | Y | Y | Y | Y | Y | Y |
| Egg 27 | A/left | Y | Y | Y | Y | Y | Y |
| | C/right | | | | | | |
| Egg 28 | C/left | | | | | | |
| | A/right | Y | Y | Y | Y | Y | Y |
| Egg 29 | C/left | | | | | | |
| | A/right | Y | Y | Y | Y | Y | Y |
| Egg 30 | A/left | Y | Y | Y | Y | Y | Y |
| | C/right | | | | | | |
| Egg 34 | C/left | | | | | | |
| | A/right | Y | Y | Y | Y | Y | Y |
| Egg 36 | A/left | Y | Y | Y | Y | Y | Y |
| | C/right | | | | | | |
| Egg 37 | C/left | | | | | | |
| | A/right | Y | Y | Y | Y | Y | Y |
| Egg 39 | A/left | Y | Y | Y | Y | Y | Y |
| | C/right | | | | | | |
| Egg 40 | C/left | | | | | | |
| | A/right | Y | Y | Y | Y | Y | Y |
| Egg 41 | A/left | Y | Y | Y | Y | Y | Y |
| | C/right | | | | | | |
| Egg 43 | C/left | | | | | | |
| | A/right | Y | Y | Y | Y | Y | Y |
| Egg 45 | A/left | Y | Y | Y | Y | Y | Y |
| | C/right | | | | | | |
| Egg 48 | C/left | | | | | | |
| | A/right | Y | Y | Y | Y | Y | Y |
| Egg 58 | A/left | Y | Y | Y | Y | Y | Y |
| | C/right | | | | | | |
| Egg 59 | C/left | | | | | | |
| | A/right | Y | Y | Y | Y | Y | Y |
| Result: | | 100% A > C | | | | | |

What is claimed is:

1. A method of demonstrating the whitening effect of an oral care composition on a stained egg comprising:

a. creating a stain solution comprising tea and dark soy sauce in about 4800 mL deionized water at room temperature;
b. placing eggs into the stain solution and boiling for 15 minutes;
c. placing the boiled eggs in a room temperature environment and allowing them to soak in the stain solution for at least 10 hours;
d. showing an egg that has been stained to at least one consumer;
e. applying an oral care composition comprising at least one high cleaning silica for stain removal on a portion of stained eggshell of the stained egg to obtain a first treated eggshell area;
f. rinsing the egg with water;
g. showing the consumer the first treated eggshell area, wherein the first treated eggshell area has an improved whitening effect as compared to untreated eggshell of the stained egg; and
h. performing a Chromatic Aberration test by determining the statistical differences by analyzing a ΔE value for differences in color;

wherein the at least one high cleaning silica is present in the oral care composition in an amount ranging from about 1% to about 30% by wt.;

wherein, the first treated eggshell area also has an improved whitening effect as compared to untreated stained egg using a Chromatic Aberration test; and wherein the ΔE value of the treated egg is greater than about 20;

and wherein the oral care composition comprises a non-peroxide whitening agent.

2. The method according to claim 1, further comprising:

applying an oral care composition that does not contain a high cleaning silica on a second portion of the stained eggshell to obtain a second treated eggshell area; and comparing the first treated eggshell area to the second treated eggshell area, wherein the first treated eggshell area has an improved whitening effect as compared to the second treated eggshell area.

3. The method according to claim 1, wherein the at least one high cleaning silica has an average particle size ranging from about 1 μm to about 20 μm.

4. The method according to claim 1, wherein the at least one high cleaning silica has an average particle size ranging from about 5 μm to about 15 μm.

5. The method according to claim 1, wherein the high cleaning silica is a precipitated silica having a pellicle cleaning ratio of greater than 85.

6. The method according to claim 5, wherein the precipitated silica has a mean particle size d50 of from 5 to 15 μm and an oil absorption of from 40 to 120 cm3/100 g silica.

* * * * *